(12) United States Patent
Vogler et al.

(10) Patent No.: US 10,159,602 B2
(45) Date of Patent: Dec. 25, 2018

(54) TECHNIQUE FOR PHOTODISRUPTIVE MULTI-PULSE TREATMENT OF A MATERIAL

(71) Applicant: Wavelight GMBH, Erlangen (DE)

(72) Inventors: Klaus Vogler, Eckental (DE); Christof Donitzky, Eckental (DE)

(73) Assignee: Wavelight GmbH (DE)

(*) Notice: Subject to any disclaimer, the term of this patent is extended or adjusted under 35 U.S.C. 154(b) by 283 days.

(21) Appl. No.: 14/785,826

(22) PCT Filed: May 7, 2014

(86) PCT No.: PCT/EP2014/059306
§ 371 (c)(1),
(2) Date: Oct. 20, 2015

(87) PCT Pub. No.: WO2015/169349
PCT Pub. Date: Nov. 12, 2015

(65) Prior Publication Data
US 2016/0166431 A1     Jun. 16, 2016

(51) Int. Cl.
*A61B 18/20* (2006.01)
*A61F 9/008* (2006.01)
*H01S 3/00* (2006.01)

(52) U.S. Cl.
CPC ........ *A61F 9/0084* (2013.01); *A61F 9/00825* (2013.01); *H01S 3/005* (2013.01);
(Continued)

(58) Field of Classification Search
CPC .. A61F 9/008; A61F 9/00802; A61F 9/00804; A61F 9/00814; A61F 9/00823;
(Continued)

(56) References Cited

U.S. PATENT DOCUMENTS

| 4,748,980 A | 6/1988 | Cremer et al. | |
| 6,099,522 A * | 8/2000 | Knopp | ................... B23K 26/04 |
| | | | 606/10 |

(Continued)

FOREIGN PATENT DOCUMENTS

| JP | 2010-075991 A2 | 4/2010 |
| JP | 2012-091233 A2 | 5/2012 |

(Continued)

*Primary Examiner* — Ahmed Farah
(74) *Attorney, Agent, or Firm* — Keiko Ichiye, Esq.

(57) ABSTRACT

Embodiments of the invention provide a method and apparatus for laser-processing a material. In the embodiments, a diffraction-limited beam of pulsed laser radiation is diffracted by a diffraction device to generate a diffracted beam. The diffracted beam is subsequently focused onto the material and is controlled in time and space to irradiate the material at a target position with radiation from a set of radiation pulses of the diffracted beam so that each radiation pulse from the set of radiation pulses is incident at the target position with a cross-sectional portion of the diffracted beam, the cross-sectional portion including a local intensity maximum of the diffracted beam. The beam cross-sectional portions of at least a subset of the pulses of the set include each a different local intensity maxi-mum. In this way, a multi-pulse application for generating a photo-disruption at a target location of the material can be implemented.

12 Claims, 2 Drawing Sheets

(52) U.S. Cl.
CPC ..... *A61B 18/20* (2013.01); *A61F 2009/00872* (2013.01); *A61F 2009/00897* (2013.01)

(58) Field of Classification Search
CPC .............. A61F 9/00825; A61F 9/00827; A61F 9/0084; A61F 9/00861; A61F 2009/00872; A61F 2009/00897
USPC ............................................ 606/4–6, 10–12
See application file for complete search history.

(56) References Cited

U.S. PATENT DOCUMENTS

| | | | | |
|---|---|---|---|---|
| 6,210,401 | B1* | 4/2001 | Lai | A61F 9/00804 351/209 |
| 6,610,049 | B2* | 8/2003 | Lai | A61F 9/008 606/12 |
| 8,137,340 | B2* | 3/2012 | Lai | A61B 18/22 606/10 |
| 8,920,407 | B2* | 12/2014 | Raksi | A61F 9/008 606/4 |
| 2009/0321398 | A1 | 12/2009 | Mourou et al. | |
| 2013/0196083 | A1 | 8/2013 | Sharma et al. | |
| 2013/0237972 | A1* | 9/2013 | Raksi | A61F 9/00825 606/6 |

FOREIGN PATENT DOCUMENTS

| | | |
|---|---|---|
| RU | 2430832 C2 | 10/2011 |
| TW | 201012580 A | 4/2010 |
| WO | 9953992 A2 | 10/1999 |
| WO | 2010/035736 A1 | 4/2010 |

\* cited by examiner

TECHNIQUE FOR PHOTODISRUPTIVE MULTI-PULSE TREATMENT OF A MATERIAL

CROSS REFERENCE TO RELATED APPLICATIONS

This application is a section 371 national stage phase of International Application No. PCT/EP2014/059306, filed 7 May 2014, titled "TECHNIQUE FOR PHOTODISRUPTIVE MULTI-PULSE TREATMENT OF A MATERIAL," which is hereby incorporated by reference in its entirety.

TECHNICAL FIELD OF THE INVENTION

The present disclosure is concerned with a technique for the photodisruptive treatment of a material using pulsed, focused laser radiation. More specifically, the present disclosure pertains to a multi-pulse scheme for generating a photo-disruption in a material. In certain embodiments, the material is a biological material including, but not limited to, human eye tissue. In other embodiments, the material is a non-biological material.

BACKGROUND

Photo-disruption refers to a specific type of interaction between a material and laser radiation incident at the material. The photo-disruption originates from a physical phenomenon called laser-induced optical breakdown (abbreviated as LIOB) and is associated with mechanical effects including, but not limited to, cavitation resulting from plasma formation in the material being irradiated with laser radiation. The photo-disruption has proven a useful damage effect to create incisions in a transparent material (i.e. transparent to the laser radiation). While the LIOB itself may be substantially confined to the focal area of the laser radiation, LIOB-induced cavitation bubbles may expand the damage area beyond the focal volume, corrupting the precision of the incisions made in the material.

SUMMARY

Photo-disruption may be seen as an intensity-driven process in that the incident laser radiation should exceed a specific intensity threshold to cause a photo-disruption in the material. The photo-disruption threshold may depend on such factors as the type of material and the wavelength and pulse width of the laser radiation. The total amount of energy necessary to trigger a photo-disruption may be applied to the material through a single packet, or pulse, of radiation (i.e. single-pulse application) or through a temporal series of separate packets, or pulses, of radiation (i.e. multi-pulse application). The series may consist of any number of pulses more than one, and the pulses of the series may have equal or different energies. It has been observed that for a multi-pulse application the energy of each pulse of the series may be smaller than the applicable threshold energy for a single-pulse application (given the same material, wavelength, pulse width and focus dimensions), yet the cumulative effect of the series of pulses may nevertheless cause a photo-disruption. It has also been observed that the damaging dimension of cavitation may be shorter for a multi-pulse application than for a single-pulse application, thus minimizing the damage area and enhancing the cutting precision.

A conventional dual-pulse application comprises the generation of a photo-disruption at each of a plurality of processing sites in a biological material wherein only one of the processing sites is irradiated with laser radiation at a time. Each processing site is irradiated with a pre-pulse of relatively lower energy and a subsequent main pulse of relatively higher energy, wherein the main pulse causes the photo-disruption to occur at the processing site being irradiated. Following the creation of a photo-disruption at one of the processing sites, a scanner moves a focal point of the laser radiation to a next processing site to apply another pair of a pre-pulse and a main pulse.

According to embodiments of the present invention, a method of laser-processing a biological or non-biological material comprises: providing a diffracted beam of pulsed laser radiation; irradiating the material at a target position with radiation from a set of radiation pulses of the diffracted beam to generate a photo-disruption at the target position, wherein each radiation pulse from the set of radiation pulses is incident at the target position with a cross-sectional portion of the diffracted beam, the cross-sectional portion including a local intensity maximum of the diffracted beam, wherein the beam cross-sectional portions of at least a subset of the pulses of the set include each a different local intensity maximum.

The method thus implements a multi-pulse application in that the target position is irradiated with radiation from a plurality of temporally offset pulses of the laser beam. Due to the diffraction of the beam, the transverse intensity distribution of each pulse exhibits a plurality (i.e. two or more) of local maxima. A photo-disruption is generated by irradiating the material in a spatially overlapping manner with a plurality of transverse pulse segments, each belonging to a temporally different pulse of the laser radiation and each including only one from the plurality of local intensity maxima of the diffracted beam. The transverse segment is also referred to herein as a cross-sectional portion of the diffracted beam. For at least a subset of the set of pulses required to achieve a photo-disruption, the beam may be displaced transversely, i.e. perpendicularly to the direction of propagation of the beam, between successive pulses of the subset. By so displacing (or: scanning) the diffracted beam in a transverse direction, each pulse of at least the subset irradiates the target position with a beam cross-sectional portion that includes a respective different local intensity maximum. In certain embodiments, the beam is transversely scanned between all pulses of the set, so that a local intensity maximum encompassed by one of the transverse segments is not encompassed by any other of the transverse segments.

By virtue of diffracting an initially diffraction-limited beam, a plurality of partial beams may be created, each being associated with a different local intensity maximum from the plurality of local intensity maxima of the diffracted beam. In certain embodiments, the partial beams may have foci lying in a common x-y plane in a x-y-z coordinate system wherein z refers to the direction of propagation of the diffracted beam and x-y refer to directions orthogonal to the z-direction. In this case, transverse scanning of the diffracted beam allows to create a two-dimensionally extended incision having a cutting plane that is parallel with respect to a x-y-plane. In other embodiments, at least some of the partial beams may have foci lying in different x-y-planes, i.e. having different z-locations. More specifically, certain embodiments may provide for a two-dimensional row and column distribution of the foci of the partial beams wherein the z-position of the foci varies when viewed in a row direction of the distribution but remains constant, or substantially constant, when viewed in a column direction of the distribution. Scanning the diffracted beam transversely in column direction may then allow to create a two-dimensionally extended incision having a cutting plane that is inclined with respect to a x-y-plane.

Owing to the diffracted beam, a plurality of target positions can be irradiated with respective transverse pulse segments at a time, wherein each of the transverse pulse segments includes a different local intensity maximum of the beam. In this way, the material can be processed simultaneously at a plurality of target positions (or: processing sites) in a temporally overlapping manner. This allows for a reduction of the overall processing time needed for completion of the desired treatment of the material, without increasing the speed of transverse scanning of the laser beam.

In certain embodiments, the beam cross-sectional portions of at least the subset are distinct (i.e. non-overlapping) when projected onto a transverse plane (i.e. transverse to the propagation direction of the laser beam). In other embodiments, at least one pair of the beam cross-sectional portions of at least the subset are partially overlapping when projected onto a transverse plane.

In preferred embodiments, the diffracted beam has a point distribution of local intensity maxima in a focal area of the beam. The point distribution may be a one-dimensional distribution or a two-dimensional distribution. The one-dimensional distribution is one of a regular and irregular distribution along a curve, wherein the curve has one of zero curvature and non-zero curvature. A curve of zero curvature can also be referred to as a straight line, whereas a curve of non-zero curvature is not straight, i.e. is curved. Exemplary curves of non-zero curvature are a spiral and a circle. In a regular distribution, adjacent local intensity maxima have substantially equal distance from each other, whereas in an irregular distribution this distance is not equal for all the local intensity maxima of the distribution. The two-dimensional distribution may be one of a matrix distribution and a distribution based on concentric circles. In certain embodiments, the matrix distribution is regular, i.e. the local intensity maxima have substantially equal mutual distance in row and column directions of the matrix. In other embodiments, the matrix distribution is irregular, i.e. the distance between adjacent local intensity maxima, whether in row direction or in column direction, is not equal everywhere in the matrix.

According to certain embodiments, at least a subset of the local intensity maxima of the diffracted beam are distributed along a line, wherein the method comprises moving the diffracted beam over the target position in the direction of the line. The line may be a straight line or it may be a curved line, e.g., a circularly curved line or a spirally curved line. A curved line may be useful, e.g., for the creation of an annular or part-annular incision (such as, e.g., a side cut in a LASIK treatment wherein the side cut extends from a stromal bed cut to the anterior corneal surface). In one embodiment, the local intensity maxima of the diffracted beam are all distributed along a single line. In an alternate embodiment, the distribution pattern of the local intensity maxima of the diffracted beam defines a plurality of mutually parallel lines, e.g., in a matrix form or in the form of a plurality of concentric circles, wherein each line comprises a different subset of local intensity maxima, wherein each subset may include the same number or a different number of local intensity maxima.

In certain embodiments, the line-distributed local intensity maxima, i.e. those local intensity maxima that are distributed along one and the same line, are arranged in order of increasing intensity value, whereby a smaller local intensity maximum is incident at the target position at a first point of time and larger local intensity maximum is incident at the target position at a second point of time that is after the first point of time. In this way, the target position is irradiated with a temporal series of radiation packets, wherein the intensity of the radiation packets increases as the radiation packets of the series arrive one after another.

According to embodiments, the line-distributed local intensity maxima are all of different intensity values, so that in the temporal series of radiation packets that are incident at the target position the intensity increases from packet to packet.

According to other embodiments, the line-distributed local intensity maxima include two or more maxima of substantially equal intensity value. In certain embodiments, the local intensity maxima distributed along one and the same line of the distribution pattern are all of substantially equal intensity value.

Irrespective of the particular intensity distribution among the local intensity maxima that are arranged along a line of the distribution pattern, the radiation from a temporally last pulse in the set of radiation pulses causes in certain embodiments a threshold for photodisruptive damage of the material to be exceeded. In other words, whether the target position is irradiated with a set of radiation pulses of mutually different intensities or whether it is irradiated with a set of radiation pulses of substantially equal intensity, the temporally last pulse of the set has in such embodiments the effect that a multi-pulse threshold for the creation of a photo-disruption in the material is exceeded.

It has been indicated above that the single-pulse intensity threshold to achieve damage through photo-disruption may be different for different materials. According to embodiments of the present invention, each local intensity maximum of the diffracted beam is below a single-pulse intensity threshold for a laser-induced optical breakdown in human eye tissue. The single-pulse intensity threshold is a threshold applicable for the generation of a LIOB and a resulting photo-disruption in human eye tissue through a single pulse of laser radiation. The human eye tissue includes, but is not limited to, one of corneal tissue, lens tissue and retinal tissue.

According to embodiments, the method of the present invention comprises: moving the diffracted beam across the material transversely with respect to a beam propagation direction in accordance with a predetermined shot pattern to deliver a pulse of laser radiation to the material in relation to each shot position, wherein a distance between adjacent shot positions corresponds to a distance between adjacent local intensity maxima of the point distribution.

In certain embodiments, the radiation from a temporally last pulse in the set of radiation pulses has highest intensity among the set. Specifically, the radiation from the temporally last pulse in the set may comprise a global intensity maximum of the diffracted beam.

The set of radiation pulses used for irradiating the material to generate a photo-disruption at the target position may consist of any number of pulses greater than one. For example, the set may consist of two, three, four or five pulses. In other embodiments, the set may comprise a substantially larger number of pulses. For example, the number of pulses may be in the two-digit or three-digit range.

The pulses of the laser radiation may have a pulse width in the range of attoseconds, femtoseconds, picoseconds or nanoseconds.

In certain embodiments, spatially adjacent local intensity maxima of the diffracted beam have a distance of no more than 20 µm or 15 µm or 10 µm or 8 µm or 6 µm or 5 µm or 4 µm or 3 µm or 2 µm in a focal area of the beam.

In another aspect, embodiments of the present invention provide an apparatus for laser-processing a material, the apparatus comprising: a laser source configured to provide a diffraction-limited beam of pulsed laser radiation; a diffraction device configured to diffract the diffraction-limited beam to generate a diffracted beam of pulsed laser radiation; a focusing device configured to focus the diffracted beam onto the material; and a controller configured to control the diffracted beam in time and space to irradiate the material at a target position with radiation from a set of radiation pulses of the diffracted beam so that each radiation pulse from the set of radiation pulses is incident at the target position with a cross-sectional portion of the diffracted beam, the cross-sectional portion including a local intensity maximum of the diffracted beam, wherein the beam cross-sectional portions of at least a subset of the pulses of the set include each a different local intensity maximum.

The diffraction device may include at least one optical grating to diffract the laser beam. Additionally or alternatively, the diffraction device may include one or more other diffractive structures including, but no limited to, an aperture, a blade, an acoustic optical modulator, and a hologram (e.g., two-dimensional or three-dimensional hologram). In certain embodiments, the diffraction device includes a DOE (Diffractive Optical Element), which has a micro-structured surface for its optical function.

Yet another aspect of the present disclosure provides a computer-program product comprising instructions that, when executed by a controller of a laser apparatus, cause the above method to be carried out.

Still another aspect of the present disclosure provides an information storage medium (such as a disc, a storage card, or a stick, for example) on which the above computer-program product is stored.

BRIEF DESCRIPTION OF THE DRAWINGS

The invention will be explained in more detail hereinafter with reference to the accompanying drawings, in which.

DETAILED DESCRIPTION OF EXAMPLE EMBODIMENTS

Figure 1:
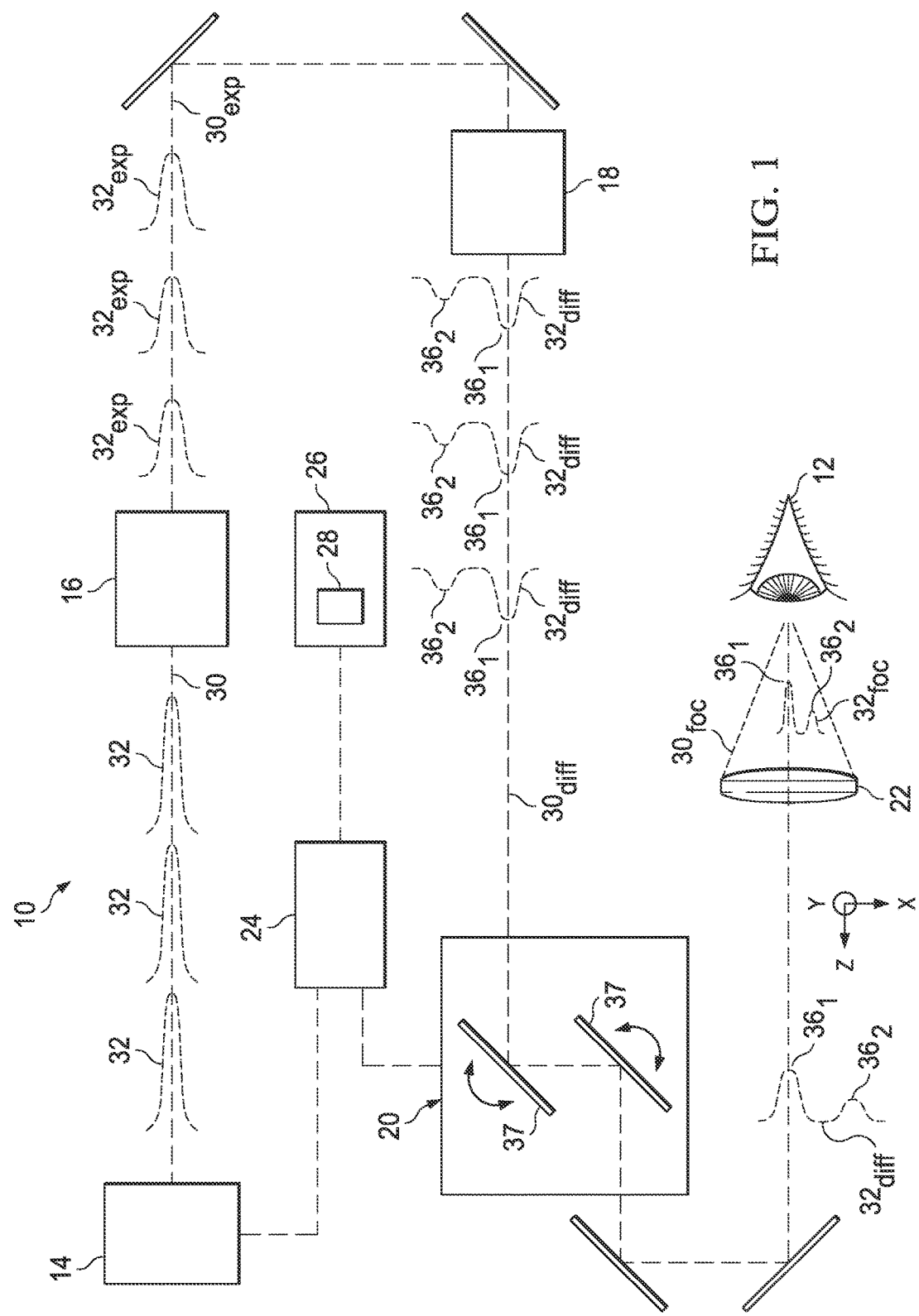
FIG. 1 schematically illustrates components of an apparatus for laser-surgical treatment of a target material according to an embodiment.

FIG. 1 shows a laser apparatus for processing a target material using pulsed, focused laser radiation, the apparatus being generally denoted 10. In an exemplary situation which is illustrated in FIG. 1, the apparatus 10 is used for performing laser surgery on a human eye 12, as may be necessary in the case of an impaired vision or a disease of the eye 12. For example, the apparatus 10 may be used for creating one or more incisions in corneal tissue, lens tissue, vitreous strands or retinal tissue of the eye 12. Such incisions may be needed as part of an operation aimed at improving a patient's vision through refractive correction. An example type of refractive eye surgery is LASIK (Laser in-situ Keratomileusis). It is needless to say that the applicability of the apparatus 10 is not limited to generating incisions in the eye 12 in the course of a LASIK operation. Other types of eye surgical operation requiring the creation of one or more incisions in the eye 12 may be equally performed using the apparatus 10, such other types of operation including, but not limited to, intracorneal lenticule extraction, keratoplasty (lamellar or penetrating), cataract surgery, etc. Moreover, the apparatus 10 may be useful for laser processing a non-living material such as in a photo-lithographical application.

The apparatus 10 may be particularly useful for applications requiring one or more strings of juxtaposed photo-disruptions to be generated in the target material in each of one or more x-y planes in a x-y-z coordinate system of the laser apparatus 10. As used herein, z refers to the longitudinal direction of the beam and x-y refers to a transverse plane with respect to the propagation direction of the beam. The string may be a rectilinear string or a curved string. A rectilinear string of photo-disruptions may be created each time the beam focus is moved along a rectilinear path portion of a serpentine scan path, which includes a plurality of rectilinear path portions extending in parallel to each other wherein adjacent ones of the rectilinear path portions are terminally connected by a reversing path portion. A serpentine scan pattern may be useful to generate a two-dimensionally extended incision in an x-y plane, e.g., a bed cut for a LASIK flap wherein the bed cut defines a stromal bed of the flap. A curved string of photo-disruptions, conversely, may be created as the beam focus is moved in an x-y plane along a curved, e.g., circular line such as may be necessary to generate in a LASIK operation a lateral incision extending from a peripheral edge of the bed cut to the anterior corneal surface.

The apparatus 10 comprises a laser source 14, a beam expander 16, a diffraction device 18, a scanner 20, a focusing objective 22, a control unit 24, a memory 26 and a control program 28 stored in the memory 26 for controlling operation of the control unit 24.

The laser source generates a diffraction-limited laser beam 30 comprised of a regular (i.e. periodic) train of pulses 32 of laser radiation. As can be seen from the schematic illustration of several of the laser pulses 32 in FIG. 1, the spatial (i.e. transverse) intensity distribution of the laser pulses 32 is Gaussian or near-Gaussian and includes a single intensity maximum. The wavelength of the laser radiation generated by the laser source 14 is suitably selected to ensure that the radiation emitted from the apparatus 10 can sufficiently penetrate into the target tissue of the eye 12 (or more general: the target material) to achieve a LIOB and a resulting photo-disruption through a multi-pulse application. For human eye treatment, for example, the laser wavelength may be in an infrared range between about 700 nm and about 1900 nm or may be in an ultraviolet range above about 300 nm. Other wavelengths may be suitable for the treatment of other materials. The pulse width of the laser pulses generated by the laser source 14 may be anywhere between attoseconds and nanoseconds and, for example, in a two-digit or three-digit femtosecond range.

The beam expander 16 expands the laser beam 30 in a manner generally known per se, using e.g., a Galilei telescope comprising a diverging lens and a converging lens arranged downstream of the diverging lens with respect to the propagation direction of the laser beam 30. The expanded laser beam output from the beam expander 16 is denoted $30_{exp}$ in FIG. 1 and is comprised of a periodic train of laser pulses $32_{exp}$. As schematically illustrated in FIG. 1, the laser pulses $32_{exp}$ of the expanded laser beam $30_{exp}$ have a larger cross-sectional area, but smaller maximum intensity than the laser pulses 32 of the diffraction-limited laser beam 30.

The diffraction device 18 is effective to diffract the expanded laser beam $30_{exp}$ to generate a diffracted laser beam $30_{diff}$. The diffracted laser beam $30_{diff}$ is comprised of a regular train of diffracted laser pulses $32_{diff}$. As schematically illustrated in FIG. 1, the diffracted laser pulses $32_{diff}$ each have a spatial (i.e. transverse) intensity distribution showing a plurality of local intensity maxima $36_i$ (with the index i taking values from 1 to N, wherein N indicates the total number of local intensity maxima of the diffracted laser pulse $32_{diff}$). The diffraction pattern, i.e. the transverse intensity distribution, is the same for all diffracted pulses $32_{diff}$ of the train. As is easy to understand, a pair of spatially adjacent local intensity maxima will be separated by a local intensity minimum (not specifically denoted in the drawings).

In the exemplary case shown in FIG. 1, the diffracted pulses $32_{diff}$ each have a total of two local intensity maxima $36_1$, $36_2$. It is to be understood that the apparatus 10 is not intended to be limited to generating diffracted laser pulses having exactly two intensity maxima. Instead, the diffraction device 18 may be configured to generate diffracted laser pulses having any number of local intensity maxima greater than two, e.g., three, four, five or six intensity maxima. These maxima may have a one-dimensional distribution pattern such as, e.g., along a rectilinear line, or a two-dimensional distribution pattern such as, e.g., a matrix pattern.

In the exemplary case shown in FIG. 1, the local intensity maxima $36_1$, $36_2$ of each diffracted pulse $32_{diff}$ have different intensities. It is to be understood that in other embodiments the local intensity maxima $36_1$, $36_2$ may be of substantially equal intensity. In general and regardless of the total number of local intensity maxima, the diffracted beam $30_{diff}$ may have a cross-sectional intensity distribution exhibiting two or more local intensity maxima of substantially equal magnitude and, alternatively or additionally, two or more local intensity maxima of unequal magnitudes.

The diffraction device 18 includes at least one diffraction member having a diffracting effect for the laser radiation as the radiation traverses the diffraction member. An exemplary diffraction member that can be used in the diffraction device 18 is a Diffractive Optical Element (DOE), which is commonly understood as referring to an optical element having a transparent substrate (e.g., a glass substrate) which has been patterned through a photo-lithographical process to have one or more micro-grating structures that are effective to convert an original beam pattern into a different beam pattern. For example, the diffraction device 18 may be configured to convert the transverse (i.e. x-y) beam pattern of the laser beam $30_{exp}$ into a dot line pattern or a dot matrix pattern of the diffracted beam $30_{diff}$, wherein each dot of the diffraction pattern includes a local intensity maximum of the diffracted beam $30_{diff}$. A holographic optical element (HOE) is another example of a diffraction member that is useful to achieve the desired diffraction effect for the laser radiation.

In embodiments not specifically shown herein, the diffraction device 18 may be disposed upstream of the beam expander 16.

The focusing objective 22 focuses the diffracted beam $30_{diff}$, resulting in a focused laser beam $30_{foc}$ (schematically indicated by dotted lines in FIG. 1). The focusing objective 22 may, e.g., be of a F-Theta type and may be a single-lens objective or multi-lens objective. The focused laser beam $30_{foc}$ is comprised of a periodic train of focused laser pulses $32_{foc}$, one of which is schematically shown for illustration purposes in FIG. 1. The repetition rate of the focused laser pulses $32_{foc}$ emitted from the apparatus 10 is in a kHz, MHz or GHz range and, for example, in a range from 50 kHz to 5 MHz or from 5 MHz to 50 MHz or from 50 MHz to 100 MHz or from 100 MHz to 500 MHz or up to a range of 1 GHz or higher.

The apparatus 10 is equipped with suitable scanning structure to allow for longitudinal adjustment of the focus position of the focused laser beam $30_{foc}$ in z-direction (i.e. in the direction of beam propagation) and to allow for transverse adjustment of the focus position in an x-y plane. For x-y scanning of the beam focus, the scanner 20 may include, in a manner generally known per se in the art, a pair of scanning mirrors 37 which are disposed to be tiltable about mutually orthogonal tilt axes, as schematically indicated in FIG. 1 inside the box representing the scanner 20. For z-scanning of the beam focus, the beam expander 16 may include an optical element (not shown in the drawings) configured to be suitably adjustable so as to impose a variable degree of divergence on the expanded laser beam $30_{exp}$. Such optical element may, e.g., be constituted of a lens of variable refractive power or a lens disposed to be positionally adjustable in the direction of beam propagation. In different embodiments, other parts of the apparatus 10 such as, for example, the scanner 20 or the focusing objective 22 may be equipped with z-scanning capability.

The control unit 24 controls the overall operation of the apparatus 10 under control of the control program 28 and particularly controls the operation of the laser source 14 and the scanning structure of the apparatus 10 including the scanner 20. The control program 28 defines a shot pattern consisting of a plurality of shot positions each represented by a set of x, y and z-coordinate values in the x-y-z coordinate system of the apparatus 10, wherein the shot pattern is so designed as to result in an incision of a desired geometry in the eye 12. Each shot position corresponds to the emission of one laser shot (i.e. one focused pulse $32_{foc}$) by the apparatus 10.

As the focus of the focused beam $30_{foc}$ is moved in transverse direction (i.e. in an x-y plane) across a target region of the eye 12 (which target region may be on an outer surface of the eye 12 or within the eye 12) in accordance with the shot pattern, the same location on or in the eye 12 is successively irradiated with radiation from a plurality of the focused pulses $32_{foc}$, and a photo-disruption is generated in the eye tissue at the location as a cumulative effect of the deposition of energy from the compound of sub-threshold pulses in the tissue. This is explained in further detail below with additional reference to FIG. 2.

Figure 2:
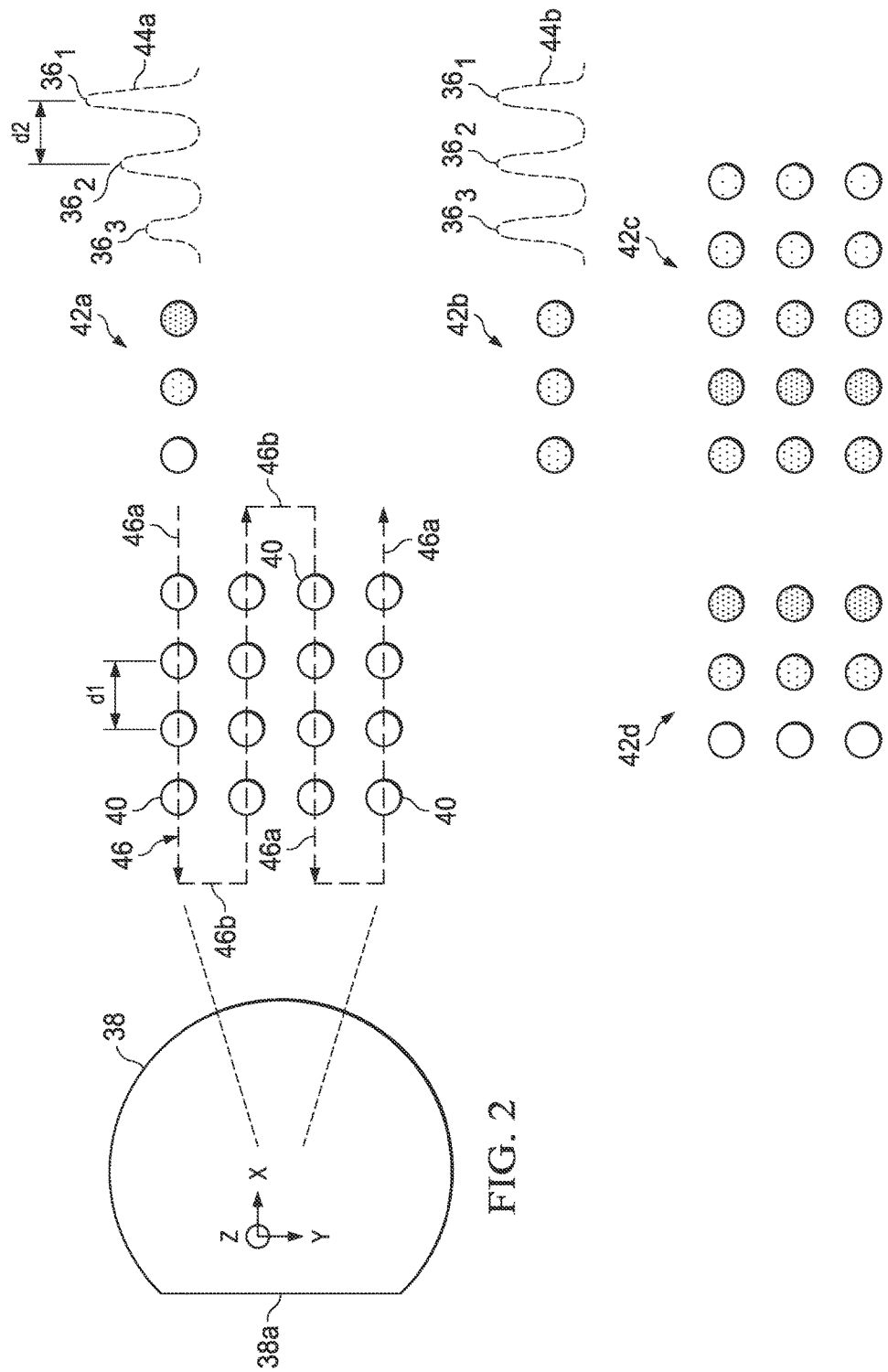
FIG. 2 schematically illustrates exemplary relationships between target positions for laser irradiation and a transverse intensity distribution of a focused laser beam emitted by the apparatus of FIG. 1.

FIG. 2 shows by way of non-limiting example an outline of a bed cut 38 in an x-y plane. The bed cut 38 is a two-dimensionally extended incision in an x-y plane and may serve to define a stromal bed for a corneal flap that is created in the cornea of the eye 12 in the course of a LASIK procedure. 38a denotes a hinge line along which the flap remains connected with surrounding corneal tissue so that the flap can be folded aside to expose underlying corneal tissue for the subsequent removal of a predefined volume of tissue using UV laser radiation (e.g., excimer laser radiation). To generate the bed cut 38, a photo-disruption is to be effected at each of a plurality of damage sites juxtaposed in an x-y plane, so that the tissue damage associated with the plurality of photo-disruptions results in the creation of the bed cut 38.

A portion of a beam shot pattern for creating the bed cut 38 is schematically visualized in FIG. 2 on the right-hand side of the bed cut 38 and includes shot positions 40 arranged in a matrix style in rows and columns. FIG. 2 further shows schematically four exemplary dot patterns 42a, 42b, 42c, 42d of the focused beam $30_{foc}$. The dot patterns 42a, 42b, 42c, 42d are a graphical tool to represent the x-y energy distribution (and hence the x-y beam pattern) of the focused beam $30_{foc}$ in the area of the beam focus; most, if not all, of the energy is concentrated in the regions represented by the dots ("dot regions") and only little, if any, radiation energy is encountered outside of these regions. Each dot pattern 42a, 42b, 42c, 42d corresponds to a different configuration of the diffraction device 18 of the apparatus 10. Every dot of a dot pattern represents a distinct cross-sectional (i.e. x-y) segment of the focused beam $30_{foc}$ and can indicate a respective local intensity maximum $36_i$ of the focused beam $30_{foc}$. In the illustrated example, different colors of the dots of a dot pattern represent different intensities of the local intensity maxima $36_i$ of the dot regions and/or may represent different energies of the dot regions. More specifically, in the illustrated example cases of FIG. 2 a black dot represents a local intensity maximum $36_i$ of larger intensity and/or a greater energy than a grey dot, and a grey dot represents a local intensity maximum $36_i$ of larger intensity and/or a greater energy than a white dot.

The dot patterns 42a, 42b are each configured as a dot line pattern, i.e. their dots are distributed along a single line, which is a rectilinear line in the illustrated example cases. For the dot patterns 42a, 42b, the focused beam $30_{foc}$ includes in each case a total of three local intensity maxima $36_i$, resulting in a total of three dots for each of the patterns 42a, 42b. In the dot pattern 42a, the dots represent local intensity maxima $36_i$ of different intensities, as indicated by the different colors of the dots of the dot pattern 42a. An associated exemplary transverse intensity distribution 44a is depicted in FIG. 2 on the right-hand side of the dot pattern 42a. As can be seen, the intensity distribution 44a exhibits local intensity maxima $36_1$, $36_2$, $36_3$ of different intensities.

In the dot pattern 42b, conversely, the dots represent local intensity maxima $36_i$ of the same, or substantially the same, intensity, as indicated by the same color for all dots of the dot pattern 42b. An associated exemplary transverse intensity distribution 44b is depicted in FIG. 2 on the right-hand side of the dot pattern 42b. As can be seen, the intensity distribution 44b exhibits local intensity maxima $36_1$, $36_2$, $36_3$ of equal intensity.

The dot patterns 42c, 42d are each configured as a dot matrix pattern, i.e. their dots are arranged in an m×n matrix having a number m of rows and a number n of columns (wherein m and n are integers greater than 1). Specifically, the dot pattern 42c is a 3×5 matrix of dots, and the dot pattern 42d is a 3×3 matrix of dots. Within a row of the matrix, the focused beam $30_{foc}$ may have local intensity maxima of equal intensity (as in the case of the dot pattern 42c) or of different intensities (as in the case of the dot pattern 42d). But each row represents the same, or substantially the same, intensity distribution as any other row of the matrix.

In certain embodiments, the x-y cross section of the focused beam $30_{foc}$ in the focal area thereof exhibits a concentration of energy to circular segments, such as illustrated by the circular shape of the dots shown in FIG. 2. It should nevertheless be pointed out that the scope of the present disclosure is in no way intended to be limited to such embodiments and that the focused beam $30_{foc}$ may exhibit in its focal area any suitable x-y distribution of energy coming with a plurality of spatially dispersed local intensity maxima. The concept of a dot pattern of the focused beam $30_{foc}$ is only used herein for the purpose of facilitating an understanding of the invention and particularly the concept of creating a photo-disruption in a target material by spatially superimposing radiation from at least partially non-overlapping transverse segments of temporally successive pulses of a diffracted laser beam.

The diameter of each dot region may be between 1 µm and 10 µm or between 2 µm and 8 µm or between 3 µm and 6 µm, and may be substantially equal to the focus diameter of an un-diffracted beam that can be generated by the apparatus 10 after removal of the diffraction device 18.

The mutual distance of adjacent shot positions 40 of the shot pattern in an x-y plane is denoted d1 in FIG. 2 and is, e.g., in a range between 1 µm and 10 µm or between 2 µm and 8 µm or between 3 µm and 6 µm. The mutual distance of adjacent local intensity maxima $36_i$ of the focused beam $30_{foc}$ (in the area of the beam focus) in an x-y plane is denoted d2 in FIG. 2 and is substantially equal to the distance d1. An x-y scan path for the focused beam $30_{foc}$ may be defined as a serpentine scan path as schematically depicted at 46 in FIG. 2, wherein the serpentine scan path 46 includes mutually parallel, rectilinear path portions 46a terminally connected by reversing path portions 46b.

Accordingly, as the focused beam $30_{foc}$ is moved across the shot positions 40 in an x-y plane according to a pre-defined scan path such as, e.g., the serpentine scan path 46, the same location on or in the eye 12 is successively irradiated with radiation from different beam cross-sectional portions from a set of pulses of the focused beam $30_{foc}$. For example, considering a diffraction pattern of the focused beam $30_{foc}$ corresponding to the dot line pattern 42a, a first pulse of the focused beam $30_{foc}$ irradiates the eye 12 at a specific location associated with one of the shot positions 40 with radiation from one of the dots, e.g. the left, white dot representing lowest peak intensity among the dots of the dot pattern 42a. As the focused beam $30_{foc}$ is moved by the distance d1 between successive pulses according to the pre-defined scan path, a subsequent second pulse of the focused beam $30_{foc}$ applies radiation from another dot of the focused beam $30_{foc}$, e.g. the middle, grey dot representing medium peak intensity, to the same location, i.e. the same shot position 40. As the focused beam $30_{foc}$ is thereafter moved yet another time by the distance d1 in accordance with the pre-defined scan path, a third pulse of the focused beam $30_{foc}$ applies radiation from a third dot, e.g. the right, black dot representing highest peak intensity, to the same location of the eye 12 and eventually causes a photo-disruption in the eye tissue at the corresponding shot position 40. Similar considerations apply when the focused beam $30_{foc}$ has an energy/intensity distribution corresponding to the dot pattern 42b.

In this way, a multi-pulse application can be implemented using the diffracted, focused beam $30_{foc}$. The photo-disruption results from the deposition of energy from different cross-sectional portions of the focused beam $30_{foc}$ in the irradiated material over a series of pulses of the beam. The necessary threshold for causing the photo-disruption may be reached using beam cross-sectional portions of different peak intensity/energy (as in the case, e.g., of the dot pattern 42a) or beam cross-sectional portions of substantially equal peak intensity/energy (as in the case, e.g., of the dot pattern 42b). In preferred embodiments, the last pulse of the series of pulses that are incident at a specific location of the irradiated material eventually triggers the photo-disruption in the material. In other words, the applicable threshold for photo-disruption is only surpassed in such embodiments with the arrival of the last pulse of the series.

Owing to the fact that the focused beam $30_{foc}$ is a diffracted beam having its energy spread over an area that covers a plurality of shot positions 40, and further owing to the fact that the focused beam $30_{foc}$ is moved in an x-y plane between successive pulses by only the distance d1, a plurality of shot positions 40 can be irradiated with radiation from the focused beam $30_{foc}$ at a time. For a given pulse repetition rate of the focused beam $30_{foc}$ and a given x-y scanning speed of the beam, this allows to reduce the overall time needed for generating a desired incision (e.g., the bed cut 38 or a posterior or anterior cut for an intra-corneal lenticule (not shown)), as compared with a conventional multi-pulse application that uses a diffraction-limited laser beam to place a plurality of successive pulses at the same shot position before scanning the beam to an adjacent shot position.

A further reduction of the overall processing time may be achieved by diffracting the laser beam to generate a matrix dot pattern such as the pattern 42c or the pattern 42d. A two-dimensional dot pattern such as the pattern 42c or the pattern 42d allows to achieve an irradiation of the target material simultaneously at shot positions 40 in a plurality of parallel lines, so that the pitch (distance) between adjacent rectilinear path portions 46a of the serpentine scan path 40 can be increased in correspondence to the number of lines of shot positions 40 covered by the matrix dot pattern. A two-dimensional dot pattern such as the pattern 42c or 42d may be generated, e.g., using a two-dimensional optical grating or a hologram.

In the dot patterns 42c, 42d, the dot regions may each represent a partial beam of the diffracted beam wherein each partial beam has an associated focus. According to certain embodiments, the foci of the partial beams all have the same, or substantially the same, z-position. According to other embodiments, the foci of the partial beams are not all in the same x-y plane. For example, in the dot pattern 42d the focus position may be constant in z-direction as one moves from partial beam to partial beam in a row direction of the matrix (i.e. horizontally in the drawing) whereas the focus position may be vary in z-direction as one moves from partial beam to partial beam in a column direction of the matrix (i.e. vertically in the drawing). Thus, while the partial beams associated with a triplet of white, grey and black dots from the same row of the matrix may have their foci located at the same z-position, the partial beams associated with the three black dots may have different z-positions of their foci (and similarly for the partial beams associated with the three grey dots and the partial beams associated with the three white dots).

The invention claimed is:

1. An apparatus for laser-processing a material, the apparatus comprising:
    a laser source configured to provide a diffraction-limited beam of pulsed laser radiation;
    a diffraction device configured to diffract the diffraction-limited beam to generate a diffracted beam comprising a set of radiation pulses, each pulse having a plurality local intensity maxima where at least two local intensity maxima have different intensity values;
    a focusing objective configured to focus the diffracted beam onto the material; and
    a controller configured to control the diffracted beam to irradiate the material at a target position with a cross-sectional portion of the diffracted beam, the cross-sectional portion including the local intensity maxima of the radiation pulses, the controlling comprising directing each radiation pulse towards the target position with the cross-sectional portion in order to distribute the local intensity maxima of the radiation pulse across the material.

2. The apparatus of claim 1, wherein the beam cross-sectional portions are distinct when projected onto a transverse plane.

3. The apparatus of claim 1, wherein at least one pair of the beam cross-sectional portions are partially overlapping when projected onto a transverse plane.

4. The apparatus of claim 1, wherein the diffracted beam has a point distribution of the local intensity maxima in a focal area of the beam.

5. The apparatus of claim 4, wherein the point distribution is a two-dimensional distribution.

6. The apparatus of claim 5, wherein the two-dimensional distribution is one of a matrix distribution and a distribution based on concentric circles.

7. The apparatus of claim 4, wherein:
    at least a subset of the local intensity maxima of the diffracted beam are distributed along a line, and
    the controller is configured to control the diffracted beam to move the beam over the target position in the direction of the line.

8. The apparatus of claim 4, wherein:
    the controller is configured to control the diffracted beam to move the beam across the material transversely with respect to a beam propagation direction in accordance with a predetermined shot pattern to generate a photo-disruption at each of a plurality of shot positions defined by the shot pattern, and
    a distance between adjacent shot positions corresponds to a distance between adjacent local intensity maxima of the point distribution.

9. The apparatus of claim 1, wherein the local intensity maxima include two or more maxima of substantially equal intensity value.

10. The apparatus of claim 1, wherein each local intensity maximum of the diffracted beam is below a single-pulse intensity threshold for a laser-induced optical breakdown in human eye tissue.

11. The apparatus of claim 1, wherein the radiation from a temporally last pulse in the set of radiation pulses has highest intensity among the set.

12. The apparatus of claim 1, wherein spatially adjacent local intensity maxima of the diffracted beam have a distance of less than 20 μm in a focal area of the beam.

* * * * *